United States Patent [19]
Heeke et al.

[11] Patent Number: 5,562,106
[45] Date of Patent: Oct. 8, 1996

[54] DENTAL APPLIANCE FOR RELIEF OF SNORING AND METHOD OF MAKING SAME

[76] Inventors: David W. Heeke, 2410 Lake Lansing Rd., Lansing, Mich. 48912; Walter Britt, 1721 Grand River, Lansing, Mich. 48906

[21] Appl. No.: 430,263

[22] Filed: Apr. 28, 1995

Related U.S. Application Data

[63] Continuation of Ser. No. 230,478, Apr. 20, 1994, abandoned.

[51] Int. Cl.$^6$ .................. A61F 5/56; A61C 5/14
[52] U.S. Cl. ................................ 128/848; 128/861
[58] Field of Search ................ 128/848, 858, 128/859–862; 2/2

[56] References Cited

U.S. PATENT DOCUMENTS

| | | | |
|---|---|---|---|
| Re. 33,442 | 11/1990 | George . | |
| D. 302,036 | 7/1989 | George | D24/34 |
| 1,146,264 | 7/1915 | Kelly | 128/861 |
| 1,674,336 | 6/1928 | King . | |
| 2,531,222 | 11/1950 | Kesling | 128/861 |
| 2,590,118 | 3/1952 | Oddo | 128/136 |
| 3,107,668 | 7/1962 | Thompson | 128/136 |
| 3,429,045 | 2/1969 | Anderson | 32/32 |
| 3,434,470 | 3/1969 | Strickland | 128/136 |
| 4,063,552 | 12/1977 | Going et al. | 128/136 |
| 4,169,473 | 10/1979 | Samelson | 128/136 |
| 4,519,386 | 5/1985 | Sullivan | 128/136 |
| 4,715,368 | 12/1987 | George | 128/136 |
| 4,856,991 | 8/1989 | Breads et al. | 433/6 |
| 4,901,737 | 2/1990 | Toone | 128/848 |
| 5,003,994 | 4/1991 | Cook | 128/848 |
| 5,056,534 | 10/1991 | Wright | 128/848 |
| 5,092,346 | 3/1992 | Hays et al. | 128/848 |
| 5,152,301 | 10/1992 | Kittelsen et al. | 128/861 |
| 5,267,863 | 12/1993 | Parker | 433/215 |
| 5,313,960 | 5/1994 | Tomasi | 128/848 |
| 5,365,945 | 11/1994 | Halstrom | 128/848 |
| 5,427,117 | 6/1995 | Thornton | 128/848 |

*Primary Examiner*—Michael A. Brown
*Attorney, Agent, or Firm*—Young and Basile, PC.

[57] ABSTRACT

A non-surgical oral appliance for improving breathing, and abating or completely alleviating snoring sounds and symptoms while sleeping. The patient is pre-tested and pre-fitted for the appliance so that appliance positions the mandible in an open position and protrusive position to hold the mouth partially open. The appliance has a right and left extension wherein each extension has upper and lower surfaces premolded to the contour of the patient's back teeth. A bridge connects the right and left extensions having been premolded to conform to the upper palate of the patient's mouth. The upper and lower surfaces of each extension are spaced to provide optimum mouth height that was pre-tested to alleviate the snoring sound. Upon insertion, the appliance facilitates an air passage for breathing and also allows the patient to talk while remaining virtually invisible to an observer.

20 Claims, 3 Drawing Sheets

5,562,106

DENTAL APPLIANCE FOR RELIEF OF SNORING AND METHOD OF MAKING SAME

This application is a continuation of Ser. No. 08/230,478 filed Apr. 20, 1994, now abandoned.

FIELD OF THE INVENTION

The invention relates to a non-surgical oral appliance and method for making same, that repositions the mandible to facilitate breathing while sleeping.

BACKGROUND OF THE INVENTION

Difficulty of breathing while sleeping often manifests itself as snoring or the more serious obstructive sleep apnea. Snoring is a condition affecting approximately 40% of the adult population, while obstructive sleep apnea affects approximately 7% of the adult population. Although snoring can occur as a result of a physical anomaly, such as enlarged tonsils or adenoids, generally, snoring occurs during sleep, because the muscles of the upper throat relax. As a person breathes, the turbulence of the air causes a flutter valve effect on the soft tissues of the upper throat. The vibration resulting from the flutter valve effect of the soft tissues of the upper throat causes snoring sounds.

Sleep apnea is due to the obstruction of the upper airway which produces short episodes of breathing stoppage that characterizes apnea. Frequent arousals during the night occur when the patient awakens in order to overcome the airway blockage. As a result, sleep apnea can cause excessive daytime sleepiness as well as high blood pressure, strokes or cardiac arrest.

Although such severe steps can be taken to alleviate snoring or the more serious condition of sleep apnea as performing a surgery, such as a tracheostomy, to ensure adequate air exchange; it is desirable to provide a treatment that is non-surgical, non-evasive, comfortable, and not unsightly. It is also advantageous to provide a treatment that the patient has prior knowledge of its effectiveness to further ensure compliance.

Currently, there are a number of therapeutic apparatus that do not require surgery. U.S. Pat. Nos. 4,715,368 and Re. 33,442 issued to George discloses an oral device to prevent the closing of the breathing passage. The oral device consists of a one-piece mouthpiece having a front beak housing with an orifice airway therein. The oral device is custom-fitted and anchored to appropriate molars with wire clasps and a guide. A disadvantage of this oral device is that it is obvious to the observer when a patient is wearing the apparatus. If a patient is self-conscious about the oral apparatus he would be disinclined to wear it and thus defeat the purpose. Another disadvantage is that flanges are used to depress and constrain the tongue of the patient to prevent the breathing passage to close. This constraint on the tongue can prove uncomfortable to the patient, and discourage its use.

U.S. Pat. No. 5,092,346 issued to Hayes and Meade discloses a dental device which grips all upper teeth forward of the pre-molars and has a downwardly extending ramp against which the lower teeth engage during sleep. An aperture in the device between the upper portion and the lower portion facilitates the passage of air for mouth breathing and attracts the tongue forward.

U.S. Pat. No. 5,003,994 issued to Cook discloses an oral device which has a rigid shell with appliance socket structure adapted to engage the upright portion of tooth and gum of either the top or bottom jaw. The device also includes a cam structure which extends downwardly and has a pliant tooth contacting material such as silicone to forcibly position the mandible forward. Similar to the Hayes and Meade device, this oral device includes a central breathing aperture.

In both of the devices disclosed in Cook and in Hayes, et al., the oral devices invade the patient's mouth to such a degree that it is obvious to both him and an observer. In order to ensure patient compliance, it is desirable to have an oral device that is both comfortable to wear and aesthetic for viewing by other household members.

Because snoring and sleep apnea may be the result of structural anomalies, such as enlarged tonsils and adenoids, or nasal polyps to name a few, it is necessary to first examine the patient before prescribing an oral device. If a structural anomaly is the cause of the breathing disorder during sleep, then surgery would be the recommended procedure.

If, in fact, the patient is not suffering from a structural anomaly, it is nonetheless necessary to determine whether the oral apparatus will, in fact, alleviate the snoring problem. It is also advantageous to provide a method and device which will assure the patient that the completed apparatus will successfully alleviate snoring before he has incurred the expense of purchasing the oral device. The prior art does not address the need for such testing.

SUMMARY OF THE INVENTION

The present invention addresses the aforementioned concerns. The present invention is a device for releasable insertion into a patient's mouth to position the mandible in a protrusive open orientation thereby providing a clear unobstructed airway and eliminating or substantially alleviating snoring. The device is composed of an FDA approved polymeric material which is flexible, lightweight and adapts to the contours of the teeth to permit a self-retentive frictional contact between the device and the associated upper or lower posterior teeth.

The device is adapted to fit over the upper four posterior teeth on both sides of the jaw and the corresponding lower posterior teeth in a deformable, flexible retentive manner. The retentive portion of the device extends upwardly toward the gum line of each respective tooth to provide a more secure fit and contact between the device and the teeth. In the first embodiment, the device also includes an upper plate-like bridge preferably composed of the same polymeric material. This plate-like bridge extends behind the front teeth over the forward portion of the upper palate to join the two respective biting surfaces.

When in position, the device provides protrusive jaw movement sufficient to open the airway and eliminate snoring sounds. To attain this, protrusive movement of the mandible can be between 0 and 10 mm, with 5 to 10 mm protrusive movement being preferred. Additionally, the device provides a vertical opening between the upper and lower jaw sufficient to permit an adequate airway. This vertical opening between the upper and lower jaw is generally between 5 and 7 mm. Since the device is adapted to fit over the four posterior teeth of the mouth, less of the device is visible to an observer. This provides a more aesthetic looking oral device that allows the patient to feel more comfortable when wearing the device, and also allows him to speak contributing to overall comfort and wearability.

In order for the oral device of the present invention to be effective, it is necessary to determine proper protrusive and vertical orientation. To do this most effectively, it is necessary to test various combinations of vertical and protrusive jaw orientations to determine the optimum for the given patient. To accomplish this, a uniquely designed bite jig is placed in the patient's mouth to orient the jaw and determine height and protrusion of the lower jaw required to abate or completely eliminate snoring sounds. The in-office testing with the bite jig will also increase the patient's confidence that his snoring can be significantly reduced or eliminated before preparing the actual apparatus.

The use of the bite jig offers a predictable indicator of successful alleviation of snoring. Testing has indicated that 85% of patients using the oral device of the present invention experience eliminated or softened snoring. Predetermination using the bite jig of the present invention can permit the practitioner and patient to ascertain that the individual will benefit appreciably from using the oral device. Sleep disorders such as sleep apnea generally must be diagnosed with a comprehensive history of the patient and a physical examination focusing on the head and neck and cardiovascular system; but the oral device may also aid in such sleep apnea disorders.

Once the proper height and protrusion is determined that eliminates snoring, the patient can be fitted for the actual oral device of the present invention. With the jig in place in the patient's mouth at the precise height and protrusion which alleviates or eliminates snoring, dental putty is inserted along the back teeth to form an impression of the faces of the teeth and the height of the opening. The jig and putty are then removed and impressions of the entire upper and lower jaw are made by conventional means. From the impressions made on the dental putty in cooperation with measurements taken by the dentist based on the height and protrusion of the jig, the device of the present invention can be made to conform exactly to the patient's mouth.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

An oral device for abating or softening snoring symptoms in approximately 85% of patients is generally indicated by numeral 10. The device is composed of a polymeric material constructed from a suitable polymeric material or combination of materials which provides a finished oral device which is flexible, light-weight, durable and capable of adapting to the contours of the wearer's teeth to permit self-retentive frictional contact between the device and the associated upper or lower teeth. The polymeric material is, preferably, a material approved by the U.S. Food and Drug Administration for use in the oral cavity. Preferably, the oral device of the present invention is composed of a polymethylmethacrylate resin independent of or in combination with a methylmethylmethacrylate resin and may also contain amine initiators, ethylene glycol and specific methacryloyloxyethanes. The polymeric material is flexible, lightweight, translucent and adapts to the contours of the teeth to permit a self-retentive frictional contact between the device and the associated upper and lower posterior teeth. The flexible material is trimmable to provide reduced retention where necessary and for more comfort; and will provide better usage by the patient over the hard plastic material of prior devices. The material is durable and easily maintained, and can be cleaned by brushing and/or soaking; by way of example, suitable polymethylmethacrylate resin powders and methyl methacrylate base resin liquids from Ivoclar North America of Amherst, NY. Specific characteristics of these materials are enumerated in Table I and Table II.

TABLE I

Characteristics of Polymethylmethacrylate Resin Powders

| Contents | % Range |
| --- | --- |
| Polymethylmethacrylate | 60–100 |
| Benzoyl Peroxide | 0.5–1.5 |
| Titanium Dioxide | 0.1–1.0 |
| Characteristics: | fine clear pink dust-like particles with no odor |

TABLE II

Characteristics of Methyl Methacrylate Resin Liquids

| Contents | % Range |
| --- | --- |
| Methyl Methacrylate | 60–100 |
| Amine Initiator | 0.1–1.0 |
| 1.2 Bis (Methacryloyloxy) Ethane | 1–5 |
| Ethylene Glycol | 1–5 |
| Boiling Point: | 100° C. |
| Vapor Pressure (mm Hg): | 29 kPa |
| Vapor Density (air = 1): | 3.46 |
| Specific Gravity ($H_2O$ = 1 g/cm$^3$): | 0.95 |
| Flash Point (°C.): | 11.5 Closed Cup |
| Appearance and Odor: | clear colorless liquid, sharp odor |

Figure 1:
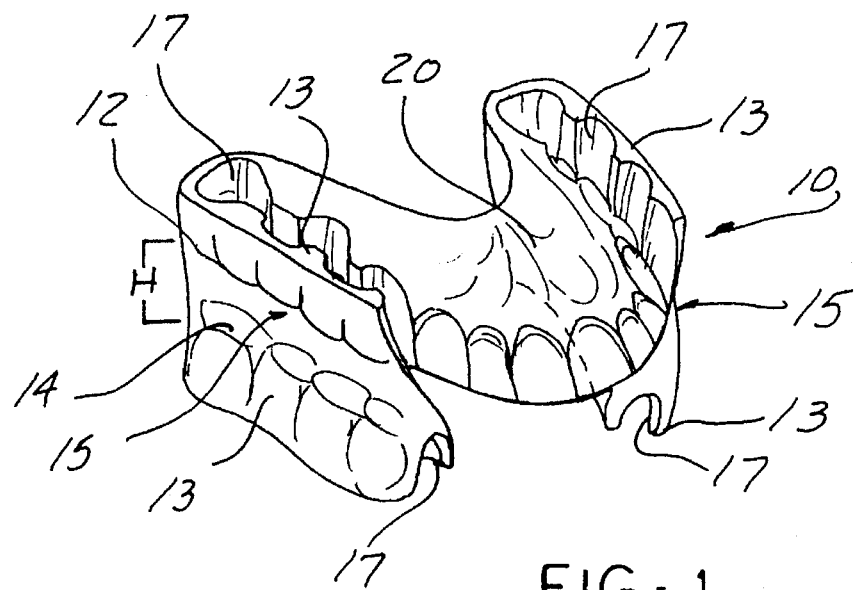
FIG. 1 is a perspective view of one embodiment of the oral device of the present invention.
Figure 2:
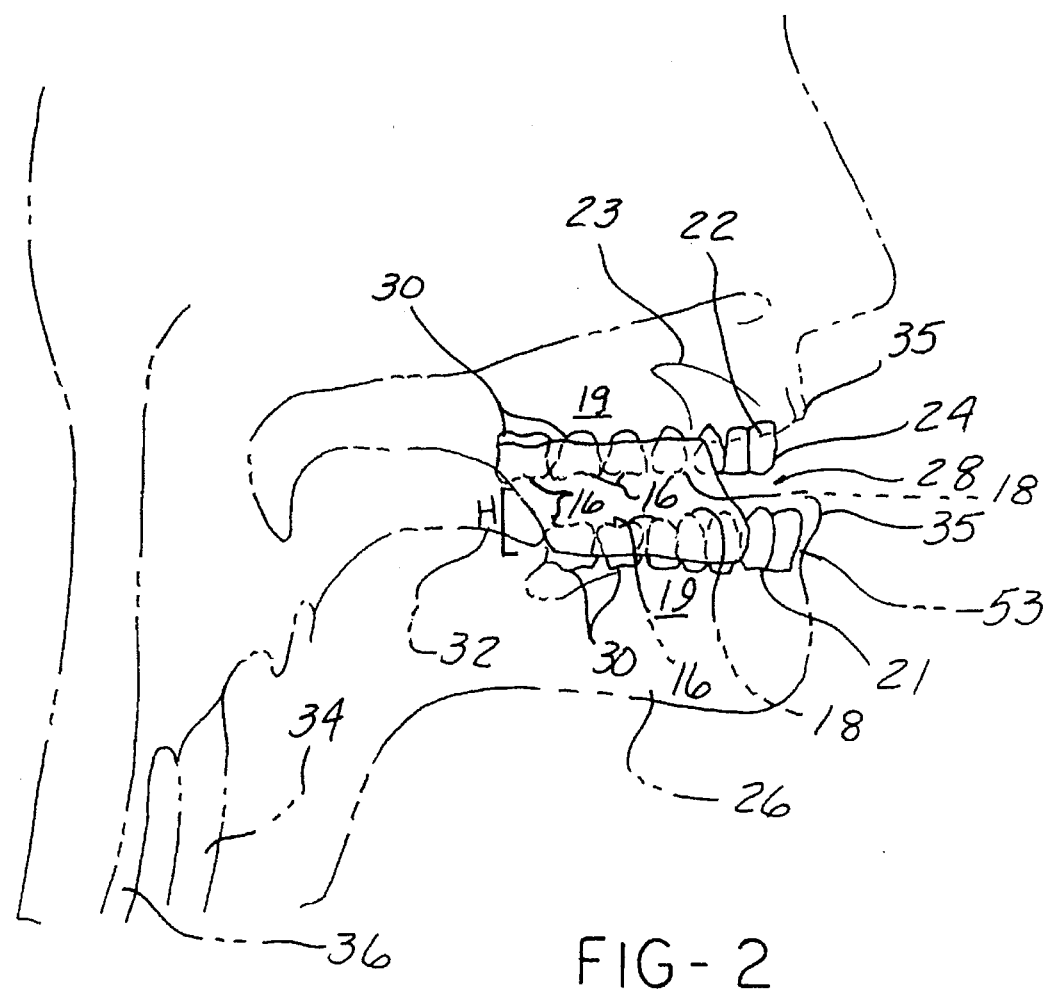
FIG. 2 is a partial elevation and cross-section of the human head and neck showing the oral device in place.

The device 10 is an individualized shell that has the upper depressions 12 and lower depressions 14 of the upper and lower four posterior teeth, which include the back molars 16 and second bicuspid 18 of the upper and lower teeth. The depressions provide biting surfaces 17 for the aforementioned teeth. A retentive portion 13 fits over the upper four posterior teeth on both sides of the jaw and the corresponding lower posterior teeth. The retentive portion 13 extends upwardly toward the gum line 19 of each respective tooth to provide a more secure fit and contact between the device 10 and the teeth. A plate-like bridge 20 conforming to the back of the maxillary anteriors 22 and the upper palate 23 of the mouth extends beyond the front teeth 24 and join the two respective biting surfaces 17. The biting surfaces are spaced at a pre-tested height (H) and protrusive jaw 26 position determined to alleviate snoring sounds. The respective biting surfaces 17 are connected by lateral surfaces 15 which extend between the biting surfaces 17 in an essentially parallel fashion and have the appropriate pretested height (H). This provides an aperture 28 in the mouth in which the patient can breathe and speak. For the patient who has an edentulous mouth, the oral device 10 can be molded to the gums where the back molars 16 and second bicuspid 18 would have been located. It is preferred that the device 10 encompasses the area of at least four back teeth, upper and lower, on each side of the mouth to provide sufficient amount of material included in the biting surface to provide adequate retentive area and to prevent a patient with the nervous disorder, bruxism from grinding on the oral device 10. As seen in FIG. 2, the retentive portion 13 of the oral device 10 extends toward the gum line 19 of each respective tooth over the super bulge 30 of each contacted tooth to provide a more secure fit and contact between the device and the teeth.

Once the oral device 10 is in place, the jaw 26 will be protruded outward which naturally forces the tongue 32 forward, thereby providing an open passageway leading to the trachea 34 and esophagus 36. The oral device 10 of the current invention does not restrain and cause discomfort to the tongue. The predetermined height (H) of the bite impressions keeps the air passage open but allows the lips 35 to be either closed or open.

Figure 3:
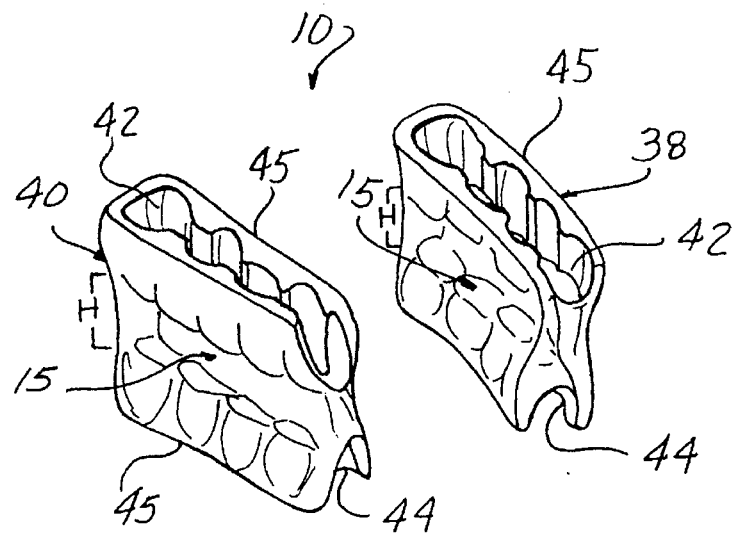
FIG. 3 is a perspective view of an alternative embodiment of the oral device of the present invention.
Figure 4:
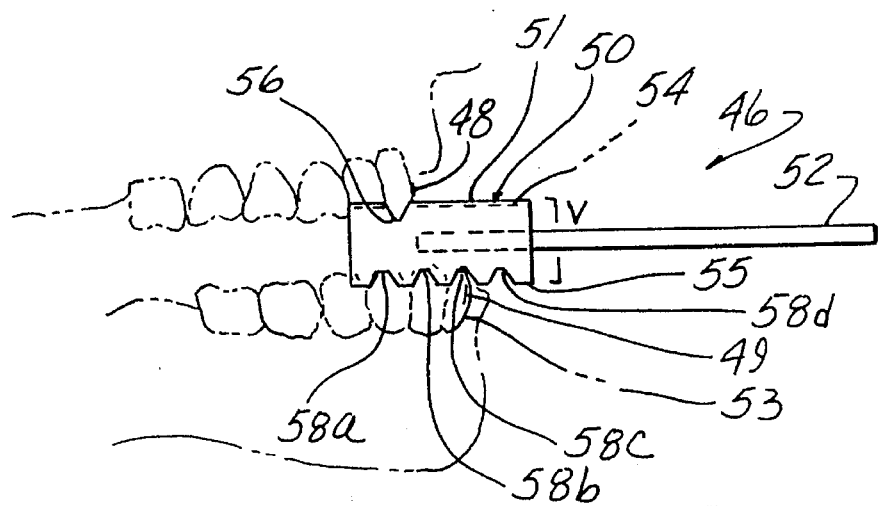
FIG. 4 is a partial elevation and cross-section of the mouth area showing a bite jig in place.
Figure 5:
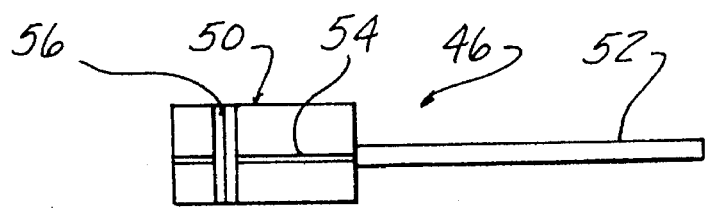
FIG. 5 is a top view of the bite jig.
Figure 6:
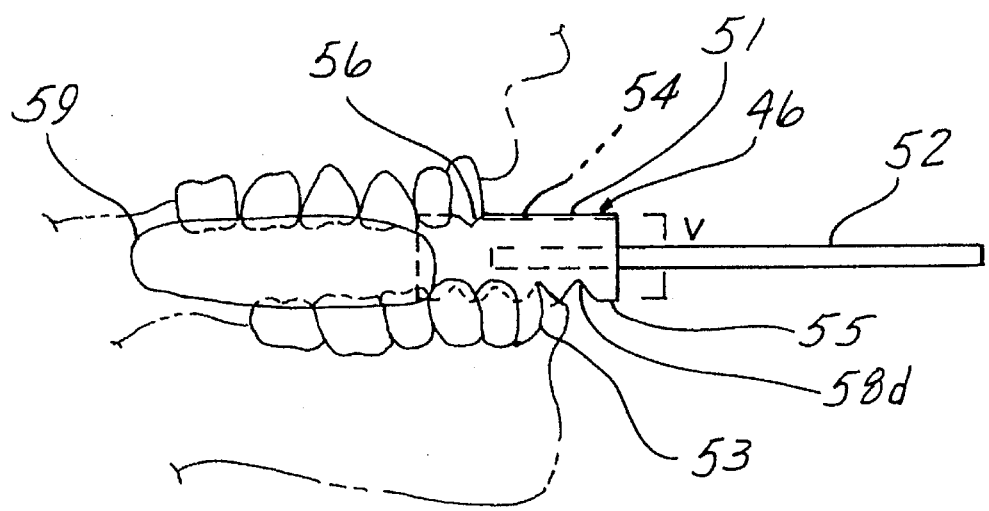
FIG. 6 is a partial elevation and cross-section of the mouth area showing dental putty and the bite jig in place.
Figure 7:
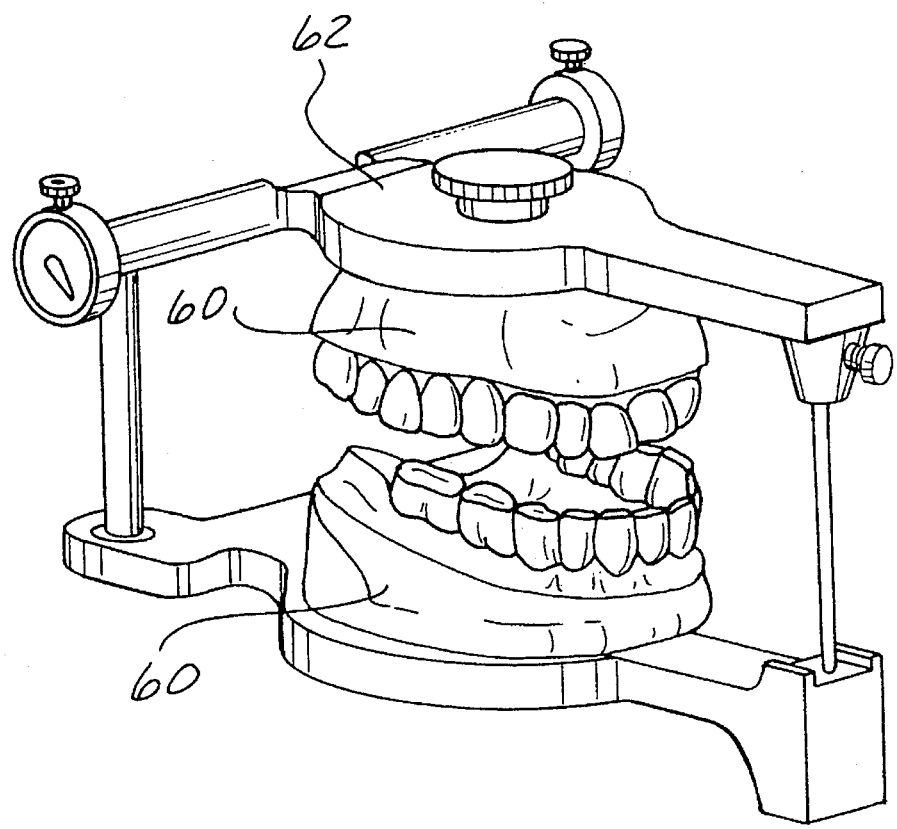
FIG. 7 is a perspective view of conventional teeth molds on an articulator.

FIG. 3 shows an alternative embodiment. This embodiment eliminates the plate-like bridge 20 and is two individualized shells 38, 40 that include the upper depressions 42 and lower depressions 44 of the back molars 16 and second bicuspid 18 of the upper and lower teeth. Retentive portions 45, again, extend over the super bulge 30 of each tooth of the upper four posterior teeth 16, 18 and the corresponding lower posterior teeth 16, 18 on each shell 38, 40. As in the first embodiment, this embodiment encompassing bilateral sections include biting surfaces 17 that are also spaced at a pre-tested height (H) and a jaw protrusion position determined to alleviate snoring sounds. When the shells 38, 40 are in place in the mouth, an aperture 28 formed by the opening between the maxillary anteriors 22 and the mandibulary anteriors 21 provide a large open airway 28 for air passage into the anterior of the mouth. Because only the back teeth 16, 18 are encapsulated by the oral device 10 leaving the upper and lower central incisors 48, 49 free; and because the material preferred for the oral device 10 is translucent, the oral device when installed in a patient's mouth is virtually invisible to an observer.

A new testing procedure and method for construction of the oral device 10 is an important aspect of the invention. An important aspect of this invention is to indicate to the patient's satisfaction that the oral device 10 will alleviate snoring sounds. It is estimated that 85% of patients who snore can be helped by this oral device 10. It is important, then, to differentiate the other 15% who should be directed to other therapeutic procedures. An in-office test procedure utilizing a bite jig 46 offers predictable results. The bite jig 46 is a small testing device that is inserted in a patient's mouth between the upper or maxillary central incisors 48 and the lower central incisors 49. The bite jig 46 is generally a rectangular box-shape device 50 having a handle 52 extending therefrom to facilitate insertion into a patient's mouth. The smallest bite jig 46 normally used has a length of 10 mm, a width of 5 mm, and a height (V) of 5 mm. On the top side 51 of the bite jig 46 is a centerline marking 54 running along the axial length as to the handle 52. Traversing the top side 51 of the jig and the centerline marking 54 is a slot 56, 2 mm from the distal end from the handle 52.

On the bottom side 55 of the bite jig 46 are multiple slots 58 (a, b, c, d) spaced along the length of the jig and parallel to the single slot 56 on the top side 51 of the jig. In the preferred embodiment, four slots 58 (a, b, c, d) are spaced 2 mm from an adjacent slot. The first slot 58a is located 2 mm from the distal end of the handle 52. The bite jig 46 has a vertical (V) size that is available in varying increments (preferably 5 mm, 7 mm, 9 mm and 11 mm) to provide various vertical openings of the mouth.

The dentist or physician will begin by using the bite jig 46 having the smallest vertical (V) opening, preferably 5 mm. Before placing the jig 46 in the patient's mouth, the dentist will request the patient to close the mouth to a normal biting position. The dentist will mark the mid-line 53 of the upper to lower central incisors with a marking device on the lower incisors 49. The dentist then places the jig 46 over the maxillary central incisors 48 so that maxillary central incisors 48 are resting in slot 56 and centerline 54 of the jig is at the mid-line of the maxillary central incisors 48. The patient will move his lower jaw 26 so that the lower central incisors 49 are located in the first slot 58a (at a distal end from the handle) on the lower side of the bite jig 46. The patient will then be requested to attempt to snore. If snoring sounds occur, the patient will be asked to protrude his lower jaw 26 forward so that his lower central incisors 49 are located in the next adjacent slot in the jig 58b. This procedure of moving the jaw forward in the jig into next adjacent slots 58a through 58d will continue until snoring sounds are relieved. If the snoring sounds are not relieved after testing in the fourth slot 58d, it will be necessary to use a bite jig 46 having a larger vertical height (V), i.e. 7 or 9 mm. The above procedure will be followed until snoring sounds have been relieved.

Once snoring sounds have been relieved, the dentist will make certain that the lower mid-line mark 53 is lined up at the centerline 54 of the jig 44. The maxillary mid-line is also checked with the centerline 54 of the jig. After the upper 48 and lower 49 central incisors are determined to be in line with the centerline 54 of the jig 46, bite putty 59 is placed between the posterior teeth, making certain that adequate putty 59 is used to completely fill interocclusal space and register occlusal surfaces of the upper and lower posterior teeth 16, 18 on right and left sides. After the bite putty 59 is set, the dentist will remove the jig 46 and bite registration formed by said putty 59. Using this procedure, the bite jig 46 provides vertical as well as protrusive measurements for positioning the mouth to alleviate snoring.

The dentist will then take accurate upper and lower alginate impressions of the patient's mouth by conventional means. At a dental lab, a model or mold 60 of the patient's mouth will be constructed in hard die stone from these impressions. The model will be placed on an articulator 62. The model 60 together with the bite registration formed by the bite putty 59 will be used to fabricate the oral device 10 of the preferred invention.

The procedure for testing and fitting the oral device can be done in two in-office appointments, taking only a half hour of the patient's time. The bite jig 46 provides predictable results to provide reinforcement to the patient that the oral device 10 will work. The material used for the oral device is flexible and pliant; and not readily visible to an observer. These are all factors to encourage compliance by a satisfied patient.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An individualized oral device removably insertable in the mouth of a patient for facilitating breathing while sleeping and to alleviate snoring, the mouth of the patient defined by a maxilla and a mandible, the maxilla and the mandible each having incisor regions, and respective right and back molar regions and right and left bicuspid regions, the device comprising:

a shell composed of a flexible material, the shell preconfigured to fit the mouth of the patient, the shell having a pair of members capable of releasably contacting and engaging an associated region in the mouth of the patient defined by the location of the molars and the second bicuspids, the members having an upper surface, an opposed lower surface, a lateral lingual surface oriented proximate to the interior of the mouth of the patient when the shell is positioned in the mouth, and an opposed outwardly oriented buccal surface, the lateral surfaces contiguous to and extending between the upper an lower surface, wherein each member extends anteriorly to the region defined by the first bicuspid and posteriorly to the region defined by the second molar and each member engages maxillary and mandibular arches of the associated molar and bicuspid regions labially and lingually, the upper and lower surfaces having depressions defined therein corresponding to the location of the, associated molar region and second bicuspid region, the upper and opposed lower depressions forming biting surfaces wherein said biting surfaces on each respective member are positioned at a fixed height and orientation sufficient to provide a vertical opening in the mouth of the patient to force the mouth open to a position that protrudes the incisor region of the mouth jaw, and thereby forms an obstruction-reduced air passage and an open gap between region defined by the lower and upper incisor teeth of the patient for breathing.

2. The oral device of claim 1 wherein the height is predetermined by a testing implement.

3. The oral device of claim 1 wherein the members of the shell has retentive portions composed of a flexible material, said retentive portions contiguously joined to said upper and lower depressions, said retentive portions adapted to deformably and releasably extend over buccal and lingual surfaces of each of the molars and bicuspids, wherein said retentive portions extend beyond the super bulge of each of the molars and bicuspids.

4. The oral device of claim 1 wherein the shell extends over the gum line of a patient having an edentulous mouth and has retentive portions composed of a flexible material, the retentive portions contiguously joined to said upper and lower depressions, said retentive portions adapted to deformably and releasably contact the gum line of said patient.

5. The oral device of claim 1 further comprising a plate-like bridge composed of a flexible material, the plate-like bridge composed of a flexible material, the plate-like bridge conforming to the back of the maxillary anteriors and the upper palate of the mouth, said bridge joining the biting surfaces.

6. The oral device of claim 1 wherein the height is sufficient to provide a vertical opening in the mouth between about 5 and about 7 mm.

7. The oral device of claim 1 wherein the mandible is maintained in a protrusive position of less than 10 mm.

8. The oral device of claim 1 wherein the mandible is maintained in protrusive position is between about 5 and about 10 mm.

9. The oral device of claim 1 further comprising a plate-like bridge conforming at least a portion of the upper portion of the mouth, the bridge Joining the biting surfaces the plate-like bridge composed of a flexible material, wherein the plate-like bridge releasably contacts an anterior section of hard palate region proximate to and extending posteriorly from free gingival margin of a lingual surface of maxillary anterior incisor teeth.

10. The oral device of claim 9 wherein the flexible shell has lingual and labial retentive portions composed of a flexible material, extending over each of the molars and bicuspids, wherein the retentive portions extend beyond the super bulge of each of the molars and bicuspids, wherein each lingual retentive portion associated with maxillary molars and bicuspids further extends onto lingual palatal tissue proximate associated molars and bicuspids.

11. An individualized oral device insertable in the mouth of a patient for facilitating breathing during sleeping and to alleviate snoring comprising:

a shell pre-configured to fit the mouth of a patient, the shell having upper and lower depressions located on a right arm and a left arm to flexibly and releasably contact back molars and second bicuspids of said patient, said upper and lower depressions forming right and left biting surfaces, said biting surfaces spaced at a height sufficient to force the mouth open to a position that protrudes the jaw and thereby forms an air passage for breathing;

wherein said sufficient height is predetermined by a testing implement comprising:

a small rectangular box-shape bite jig sized to fit in a mouth and having a handle extending therefrom to facilitate insertion into said mouth;

said bite jig having a top side and a bottom side;

said top side having a slot traversing the top side, near a distal end from the handle, said slot adapted to fit on upper central incisors; and said bottom side having a plurality of slots adapted to fit on lower central incisors traversing the bottom side and parallel to the slot on the top side, wherein said plurality of slots are spaced at known increments.

12. The bite jig of claim 11 further comprising:

a predetermined vertical height; and a centerline running along the axial length to the handle on the top side of said jig for aligning the lower central incisors to the upper central incisors.

13. A method of making the oral device that repositions the mandible to facilitate breathing while sleeping and alleviate snoring, comprising the steps of:

obtaining measurements of the condition when snoring is alleviated, by using a bite jig, said bite jig having a known vertical height, said bit jig sized to fit in a mouth and having a handle extending from one end of said jig to facilitate insertion into the mouth, said bite jig having a top side and a bottom side near a distal end from the handle, said top side having a slot traversing the axial length, said slot adapted to fit on maxillary central incisors, said bottom side having a plurality of slots parallel to the slot on the top side, wherein each slot on the bottom side is adapted to fit on lower central incisors, and the plurality of slots on the bottom side are spaced at known increments, said measurement obtaining step comprising:

(a) placing the jig in the mouth so that the maxillary central incisors are inserted in the top slot and the lower central incisors are in the first bottom slot distal from the handle;

(b) requesting the patient to make snoring sounds;

(c) if snoring sounds are made, incrementing the lower central incisor into the adjacent bottom slot to move the jaw forward and repeating step (b);

(d) if snoring sounds are made and the lower central incisors are in the last bottom slot, getting another jig with a larger vertical height than previously used and then repeating steps (a) through (c); and (e) placing means for obtaining height and bite registration when snoring sounds are alleviated between the posterior teeth;

making accurate upper and lower alginate impressions of the mouth to construct a mold of said mouth through conventional means; and fabricating the oral device from the measurements and mold.

14. The method of claim 13 wherein getting measurements of the condition when snoring is alleviated further comprises the step of:

placing bite putty between the posterior teeth to form a bite registration when snoring sounds are alleviated.

15. A method for making the oral device that repositions the mandible to facilitate breathing while sleeping and alleviate snoring, comprising the steps in order of:

(a) requesting the patient to close the mouth to a normal biting position;

(b) making a midline mark of the upper to lower central incisors;

(c) choosing a bite jig with a known small vertical height, wherein the bite jig comprises a small rectangular box-shaped jig sized to fit in the mouth having a handle extending therefrom, and having a top side and a bottom side, said top side having a slot traversing the axial length and said bottom side having a plurality of slots traversing the bottom side and parallel to the top slot wherein said plurality of slots are spaced at known increments;

(d) inserting the bite jig into the mouth by placing the top slot over the upper central incisors so that the centerline of the jig is at the midline mark upper and the lower central incisors are placed in the first bottom slot distal from the handle;

(e) requesting the patient to make snoring sounds;

(f) incrementing the lower central incisor into the adjacent bottom slot to move the jaw forward and repeating step (e), if snoring sounds are made;

(g) choosing a bite jig with a larger vertical height than previously used and returning to step (d), if snoring sounds are made and the lower central incisors are in the last bottom slot;

(h) rechecking midline mark of the central incisors and the centerline of the bite jig;

(i) placing bite putty between the posterior teeth, wherein adequate putty is used to completely fill interocclusal space to register occlusal surfaces of the upper and lower teeth on right and left sides;

(j) allowing the putty to set to form a bite registration;

(k) removing the bite jig and bite registration formed by the putty from the mouth;

(l) taking accurate upper and lower impressions of the mouth by conventional means to construct a model of the impressions; and (n) fabricating the oral device with the aid of the model of the mouth and bite registration.

16. A device for use in a mouth of a patient for facilitating breathing while sleeping and to alleviate snoring comprising:

a pair of shell members each shell member composed of a flexible polymeric material, the shell members each having an upper surface and an opposed lower surface with depressions defined therein, said depressions forming biting surfaces which conform to and releasably contact a region of the mouth defined by the location of maxillary and mandibular posterior teeth from mesial surface of each respective first bicuspid to distal surface of each respective second molar, each shell member further having opposed extensions projecting from the biting surfaces to releasably cover and retain buccal and lingual surfaces of associated teeth wherein said biting surfaces are spaced at a height sufficient to maintain the mouth open to a position that protrudes the jaw to a position less than about 10 mm and forms an obstruction-reduced air passage and an open aperture between the incisors of the patient to facilitate breathing.

17. The oral device of claim 16 wherein the space between biting surfaces is sufficient to provide a vertical opening in the mouth between about 5 and about 7 mm.

18. The oral device of claim 16 wherein the protrusive position is between about 5 and about 10 mm.

19. The oral device of claim 16 further comprises a plate-like bridge conforming to at least a portion of the upper portion of the mouth, the bridge joining the biting surfaces; the plate-like bridge composed of a flexible material, wherein the plate-like portion releasably contacts an anterior section of hard palate region proximate to and extending posteriorly from free gingival margin of the lingual surface of maxillary anterior incisor teeth.

20. The oral device of claim 19 wherein the plate-like bridge extends between lingual retentive portions adapted to extend over lingual palatal tissue.

* * * * *